(12) United States Patent
Otsubo et al.

(10) Patent No.: US 7,530,971 B2
(45) Date of Patent: May 12, 2009

(54) DISPOSABLE PULL-ON WEARING ARTICLE

(75) Inventors: Toshifumi Otsubo, Kagawa (JP); Shunsuke Takino, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 69 days.

(21) Appl. No.: 11/469,079

(22) Filed: Aug. 31, 2006

(65) Prior Publication Data

US 2007/0016157 A1   Jan. 18, 2007

Related U.S. Application Data

(63) Continuation of application No. 10/474,252, filed as application No. PCT/JP02/04049 on Apr. 23, 2002, now Pat. No. 7,172,583.

(30) Foreign Application Priority Data

Apr. 23, 2001  (JP) .............................. 2001-125001
Apr. 19, 2002  (JP) .............................. 2002-118226

(51) Int. Cl.
    *A61F 13/15*  (2006.01)
(52) U.S. Cl. ........................... 604/385.201; 604/385.19
(58) Field of Classification Search ............ 604/385.19, 604/385.201
    See application file for complete search history.

(56) References Cited

U.S. PATENT DOCUMENTS

| | | | |
|---|---|---|---|
| 3,196,874 A | 7/1965 | Hrubecky | |
| 3,211,147 A | 10/1965 | Pherson et al. | |
| 3,744,494 A | 7/1973 | Marsan | |
| 3,848,595 A | 11/1974 | Endres | |
| 3,924,627 A | 12/1975 | Nystrand | |
| 3,968,799 A | 7/1976 | Schrading | |
| 4,661,102 A | 4/1987 | Shikata et al. | |
| 4,966,286 A | 10/1990 | Muckenfuhs | |
| 5,036,978 A | 8/1991 | Frank et al. | |
| 5,054,619 A | 10/1991 | Muckenfuhs | |
| 5,361,905 A | 11/1994 | McQueeny et al. | |
| 5,746,730 A | 5/1998 | Suzuki et al. | |
| 5,934,470 A | 8/1999 | Bauer et al. | |
| 5,967,665 A | 10/1999 | MacDonald et al. | |
| 6,010,490 A | 1/2000 | Freeland et al. | |
| 6,079,562 A | 6/2000 | Bauer et al. | |
| 6,102,892 A * | 8/2000 | Putzer et al. ........... | 604/385.01 |
| 6,165,160 A | 12/2000 | Suzuki et al. | |
| 6,666,851 B2 | 12/2003 | Otsubo et al. | |
| 2004/0133178 A1 | 7/2004 | Otsubo et al. | |
| 2004/0260264 A1 | 12/2004 | Otsubo | |

FOREIGN PATENT DOCUMENTS

EP    0951890 A2    4/1999
EP    0951886       10/1999

(Continued)

*Primary Examiner*—Tatyana Zalukaeva
*Assistant Examiner*—Lynne Anderson
(74) *Attorney, Agent, or Firm*—Lowe Hauptman Ham & Berbner, LLP

(57) ABSTRACT

A disposable pull-on wearing article includes front and rear waist regions, a crotch region extending between the waist regions, a chassis and an absorbent panel. The article has first and second tuckable side zones folded along first and second imaginary tuckable guide lines and tucked the article.

2 Claims, 13 Drawing Sheets

FOREIGN PATENT DOCUMENTS

| | | |
|---|---|---|
| EP | 1346713 | 9/2003 |
| GB | 2253131 A | 9/1992 |
| JP | 473673401 | 12/1972 |
| JP | 4820638 | 3/1973 |
| JP | 5021845 | 3/1975 |
| JP | 576565 | 3/1993 |
| JP | 11104177 | 4/1999 |
| JP | 11155904 | 6/1999 |
| JP | 11299828 | 11/1999 |
| JP | 200051273 | 2/2000 |
| JP | 200235033 | 2/2002 |
| WO | 0296333 | 5/2002 |

* cited by examiner

DISPOSABLE PULL-ON WEARING ARTICLE

The present application is based on, and claims priority from, JP Application Number 2001-125001, filed Apr. 23, 2001; JP Application Number 2002-118226, filed Apr. 19, 2002; and PCT Application Number JP02/04049, filed Apr. 23, 2002; and is a continuation application of U.S. patent application Ser. No. 10/474,252 filed Oct. 8, 2003.

TECHNICAL FIELD

This invention relates to disposable pull-on wearing articles for absorption and containment of bodily discharges.

BACKGROUND ART

Conventional disposable pull-on wearing articles such as diapers and training pants have front and rear waist regions opposed to each other and a crotch region extending between the waist regions and generally comprise a liquid-pervious inner sheet, a liquid-impervious outer sheet and a liquid-absorbent panel/core disposed between these two sheets extending across the crotch region into the front and rear waist regions to define a waist-hole and a pair of leg-holes.

In such conventional articles, transversely opposite side edges of the crotch region delineate circular arcs which are convex inwardly in a transverse direction of the article so that a transverse dimension of the crotch region is smaller than that of the front and rear waist regions and the article has a generally hourglass-shape as viewed in its unfolded state with the front and rear waist regions disjoined from each other. In this article, portions of the inner and outer sheets extending outwardly beyond the side edges of the panel/core in the transverse direction form a pair of side flaps to define leg-holes. Such wearing article is disclosed, for example, in Japanese Patent Application Nos. 1999-104177A and 1999-155904A.

If the transverse dimension of the crotch region in such wearing article of prior art is larger than that of the wearer's crotch area between its thighs, the crotch region will not be properly placed against the wearer's crotch area and particularly the panel/core which conventionally has stiffness higher than that of the inner and outer sheets and a given thickness will inevitably become bulky and may create a feeling of discomfort against the wearer when is worn. To place the crotch region of the article properly in close contact with the wearer's crotch area, it may be contemplated that the crotch region is dimensioned to be equal to or smaller than the wearer's crotch area. However, the transverse dimension of the panel/core would be reduced in the crotch region as the transverse dimension of the crotch region is reduced, so the function to absorb bodily discharges in the crotch region would be unacceptably reduced, increasing an anxiety that leakage of bodily discharges might occur in the crotch region.

In average, the transverse dimension of the wearer's crotch area is in a range of 30-80 mm. In most of the wearing articles currently available in the market, the minimum transverse dimension of the core in the crotch region is dimensioned to be in a range of 100-200 mm and the transverse dimension of the crotch region inclusive of the side flaps is dimensioned to be in a range of 150-300 mm. In this manner, the transverse dimension of the crotch region is larger than the transverse dimension of the wearer's crotch area.

It is an object of this invention to provide a pants-type disposable wearing article improved so that its crotch region can be properly placed in close contact with a wearer's crotch area without any feeling of discomfort against the wearer and leakage of bodily discharges in the crotch region.

DISCLOSURE OF THE INVENTION

A disposable pull-on wearing article comprises:

a flexible chassis including a body facing side, a garment facing side opposed to the body facing side, a front waist region, a rear waist region opposed to the front waist region, a crotch region between the front and rear waist region, a waist hole and a pair of leg-holes;

a semi-stiff, liquid-absorbent panel having first and second side edges opposed to each other, and first and second end edges opposed to each other;

first and second tuckable side zones each having one of a generally trapezoid and a generally triangle defined by a pair of oblique side and a base in both sides of the crotch region, with apexes of the first and second tuckable side zones opposed to each other, and with the bases of the first and second tuckable side zones located along the first and second side edges of the absorbent panel, respectively; and the first and second tuckable side zones being folded along the oblique sides thereof and tucked from the leg-holes into the article.

PREFERRED EMBODIMENTS OF THE INVENTION

Details of a disposable pull-on wearing article according to this invention will be more fully understood from the description given hereunder in reference to the accompanying drawings.

Figure 1:
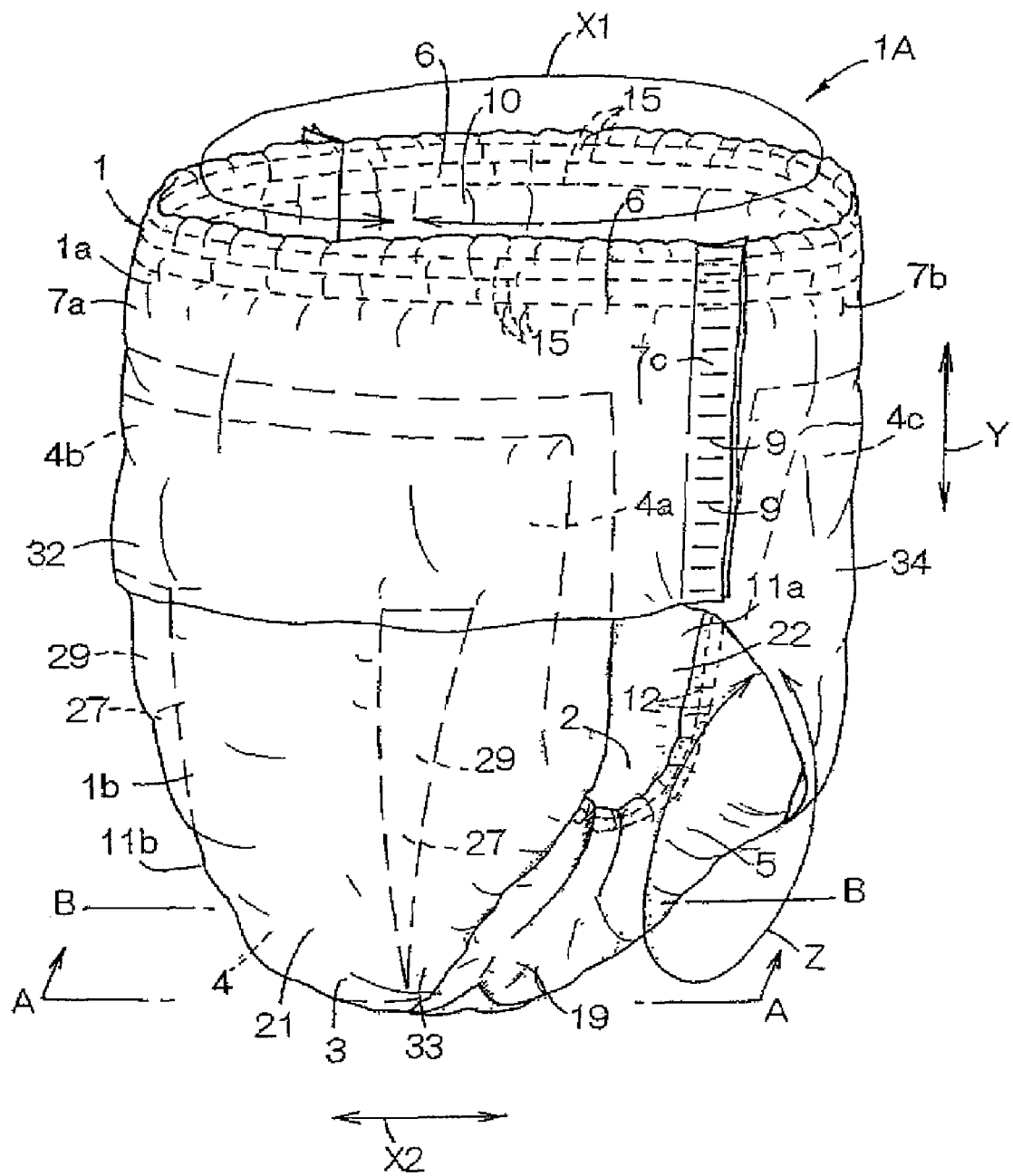
FIG. 1 is a perspective view showing one example of a disposable pull-on wearing article according to this invention.
Figure 2:
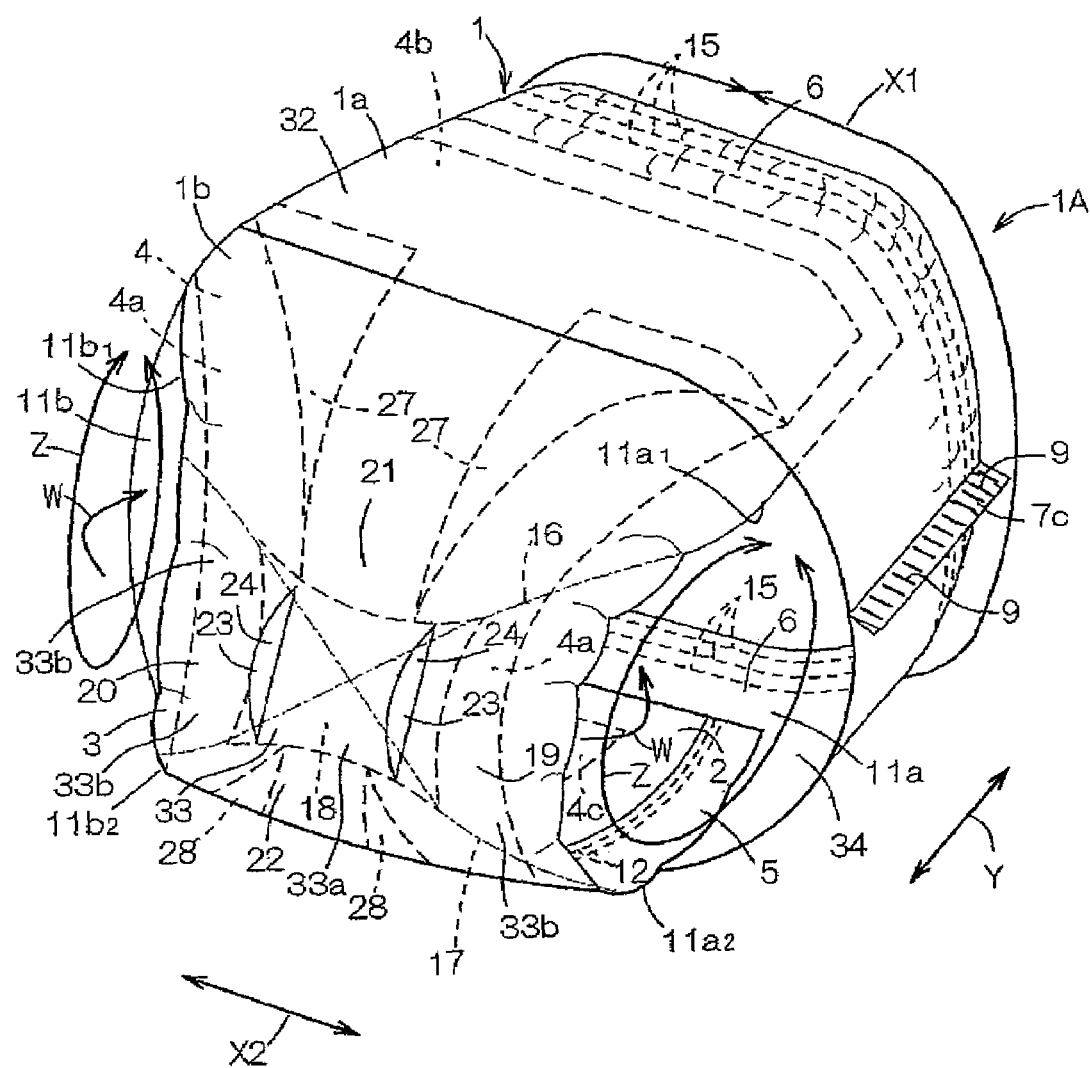
FIG. 2 is a perspective view showing the article of FIG. 1 before the first and second tuckable side zones are tucked from left and right leg-holes into the article.
Figure 3:
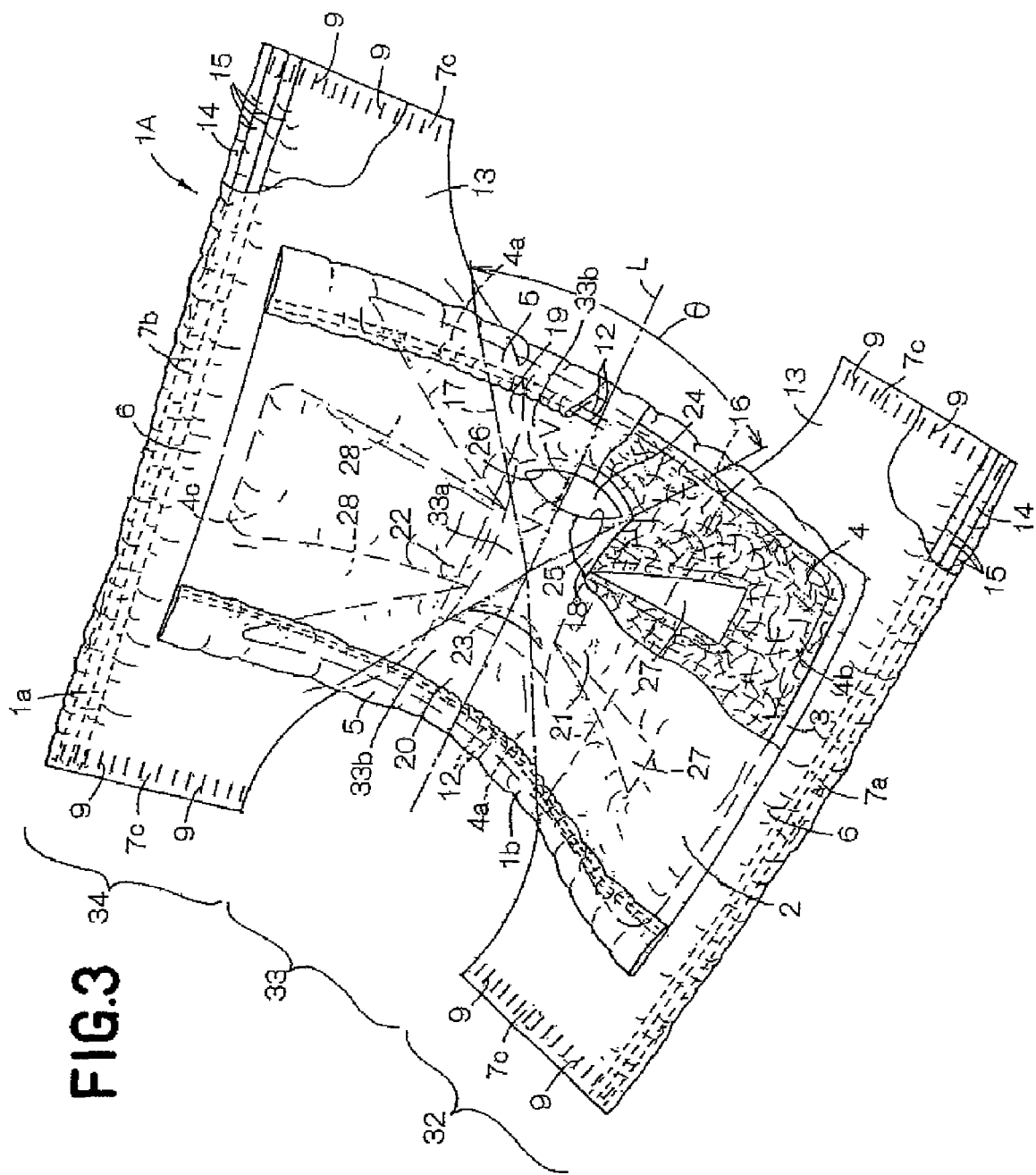
FIG. 3 is an exploded perspective view showing the article in FIG. 2 with a waist member disconnected from each other as partially cutaway.

FIG. 1 is a perspective view of a disposable pull-on wearing article 1A as an embodiment of this invention, FIG. 2 is a perspective view showing the article 1A before first and second tuckable side regions 19, 20 are tucked from a pair of leg-holes into the article 1A and FIG. 3 is an exploded perspective view showing the article 1A in FIG. 2 with a waist member 1a disjoined from its side edges as partially cutaway. In FIGS. 1 and 2, a waist surrounding direction is indicated by an arrow X1, a transverse direction is indicated by an arrow X2, a longitudinal direction is indicated by an arrow Y and a thigh surrounding direction is indicated by an arrow Z. FIG. 3 shows a state before darts are formed in the first tuckable region 19.

The article 1A comprises a flexible chassis 1 and a semi-stiff, liquid-absorbent panel 4. The chassis 1 includes a waist member 1a and a crotch member 1b. The crotch member 1b includes a liquid-pervious inner sheet 2 defining a body facing side and a liquid-impervious outer sheet 3 defining a garment facing side. The absorbent panel 4 is interposed between the inner and outer sheets 2, 3 and joined to the inner surface of at least one of these two sheets 2, 3. The waist member 1a is composed of a front portion 7a and a rear portion 7b.

The article 1A is composed of front and rear waist regions 32, 34 opposed to each other and a crotch region 33 extending between these waist regions 32, 34. The article 1A further has a pair of side flaps 5 formed by portions of the chassis 1 lying outside transversely opposite side edges 4a of the absorbent panel 4 so as to extend in the thigh-surrounding direction, respectively, and a pair of end flaps 6 formed by portions of the chassis 1 lying outside longitudinally opposite front and rear ends 4b, 4c of the absorbent panel 4 so as to extend in the waist-surrounding direction in the front and rear waist regions 32, 34, respectively.

The waist member 1a is formed of breathable sheets and extend in the waist-surrounding direction so as to surround upper portions of the crotch member 1b which is curved in a U-shape. The waist member 1a has its middle zones, as viewed in the waist-surrounding direction, joined to the outer surface of the outer sheet 3 in the front and rear waist regions 32, 34, respectively. Transversely opposite side edge zones 7c of the waist member 1a extending in the longitudinal direction are joined together by means of a plurality of heat-sealing lines 9 arranged intermittently in the longitudinal direction. By such joining, a waist-hole 10 and a pair of leg-holes 11a, 11b are formed. The article 1A is dimensioned so that each of the front and rear portion 7a, 7b of the waist member 1a has a width larger than a width of the crotch member 1b before provided with the waist member 1a, the article 1A has generally hourglass-shape as viewed in its plan view.

The absorbent panel 4 extends across the crotch region 33 into the front and rear waist regions 32, 34. The absorbent panel 4 comprises a mixture of fluff pulp and super-absorbent polymer particles or a mixture of fluff pulp, super-absorbent polymer particles and thermoplastic synthetic resin fibers compressed to a desired thickness. Accordingly, the absorbent panel 4 has stiffness higher than that of the chassis 1 including the inner and outer sheets 2, 3. It is preferred that the absorbent panel 4 is entirely wrapped with a liquid-pervious sheet such as a tissue paper or hydrophilic fibrous nonwoven fabric in order to prevent the absorbent panel 4 from being deformed from its initial shape and/or the polymer particles from falling off from the absorbent panel 4. The polymer particles may be selected from a group of materials including starch- or cellulose-based polymer particles or synthetic polymer particles.

The side flaps 5 in the crotch region 33 are respectively provided with elastic members 12 each comprising a plurality of elastic strands extending in the thigh-surrounding direction and secured to the inner surface of the inner sheet 2 in a stretched state so that the elastic members 12 are associated with the respective leg-holes. The side flaps 5 in the crotch region 33 are tucked inwardly along the side edges 4a of the absorbent panel 4 into the article 1A. Portions of the side flaps 5 respectively lying in the front and rear waist regions 32, 34 are collapsed inwardly in the transverse direction of the article 1A and joined to the respective end flaps 6 in such a collapsed state.

Though not illustrated, it is also possible to form the side flaps 5 by a sheet provided separately of the inner and outer sheets 2, 3 and to attach the sheet to the portion of the outer sheet 3 extending outwardly beyond the side edges 4a of the absorbent panel 4. In this case, the separate sheet forming the side flaps 5 may be selected from a group of materials comprising a substantially liquid-impervious and a hydrophobic fibrous nonwoven fabric and a composite sheet in the form of a laminate of hydrophobic fibrous nonwoven fabric and liquid-impervious plastic film.

Each of the waist member 1a of the chassis 1 is formed of a composite nonwoven fabric composed of two layers 13, 14 of stretchable and hydrophobic fibrous nonwoven fabric. The waist member 1a is provided along respective ends thereof with elastic members 15 each comprising a plurality of elastic strands extending in the waist-surrounding direction and secured thereto in a stretched state so as to be associated with the waist-hole. The elastic members 15 associated with the waist-hole are interposed between the layers 13, 14 of nonwoven fabric and secured to the layers 13, 14 of nonwoven fabric.

The crotch region 33 has a transversely middle zone 33a and transversely opposite side zones 33b. As indicated by single-dot-chain lines in FIGS. 2 and 3, the crotch region 33 is formed with a first imaginary tuckable guide line 16 and a second imaginary tuckable guide line 17 intersecting each other in the transversely middle zone 33a. The crotch region 33 is formed in its transversely middle zone 33a with a tuckable guide middle zone 18 which is a low stiffness middle zone. The low stiffness middle zone 18 is defined by partially removing the absorbent panel 4. The low stiffness middle zone 18 has stiffness lower than that in the remaining zone of the article 1A in which the absorbent panel 4 is interposed.

The first imaginary tuckable guide line 16 extends from a peripheral edge 11a1 of the left leg-hole 11a lying in the front waist region 32 toward a peripheral edge 11b2 of the right leg-hole 11b lying in the rear waist region 34. The second imaginary tuckable guide line 17 extends from a peripheral edge 11b1 of the right leg-hole 11b lying in the front waist region 32 toward a peripheral edge 11a2 of the left-hole 11a lying in the rear waist region 34.

The crotch region 33 is divided into first tuckable side zone 19 having a generally trapezoid defined by the peripheral edge of the left leg-hole 11a and first and second imaginary tuckable guide lines 16, 17, second tuckable side zone 20 having a generally trapezoid defined by the peripheral edge of the right leg-hole 11b and the first and second imaginary tuckable guide lines 16, 17, a front zone 21 defined between the first and second imaginary tuckable guide lines 16, 17 and a part of the front waist region 32 and a rear zone 22 defined between the first and second imaginary tuckable guide lines 16, 17 and a part of the rear waist region 34.

The first and second tuckable side zones 19, 20 are formed with a pair of darts 23 extending in the thigh-surrounding direction in a curved state. Referring to FIG. 3, an area 24 to form the dart 23 is provided in the first tuckable side zone 19. The area 24 is defined between a joining line 25 delineating a circular arc which is convex inwardly in the transverse direction of the article 1A and a joining line 26 delineating a circular arc which is convex outwardly in the transverse direction of the article 1A so as to have a spindle-shape. Each of the darts 23 can be formed by drawing the joining lines 25, 26 near to each other in the direction indicated by an arrow V and by joining the lines 25, 26 inclusive of the vicinity thereof to each other. Having formed with the darts 23, the areas 24 in the first and second tuckable side zones 19, 20 extend downwardly in the longitudinal direction of the article 1A.

Inside the transversely opposite side edges 4a of the absorbent panel 4, a pair of tuckable guide front zones 27 and a pair of tuckable guide rear zones 28 are formed. The tuckable guide front zones 27 are defined between the transversely middle zone 33a of the crotch region 33 and the front end 4b of the absorbent panel 4 lying in the front waist region 32 and extend from tuckable guide middle zone 18 toward the front end 4b of the absorbent panel 4 in the thigh-surrounding direction. The tuckable guide rear zones 28 are defined between the transversely middle zone 33a of the crotch region 33 and the rear end 4c of the absorbent panel 4 lying in the rear waist region 34 and extend from the tuckable guide middle zone 18 toward the rear end 4c of the absorbent panel 4 in the thigh-surrounding direction. The tuckable guide front and rear zones 27, 28 are respectively low stiffness zones which are defined by partially removing absorbent panel 4. The low stiffness zones 27, 28 have stiffness lower than that in the remaining zone of the article 1A in which the absorbent panel 4 is interposed.

The first and second tuckable side zones 19, 20 are folded along the first and second imaginary tuckable guide lines 16, 17 so that the first and second tuckable side zones 19, 20 may be interposed between the front and rear zones 21, 22 and thereby the first and second tuckable side zones 19, 20 are tucked together with the darts 23 inwardly in the transverse direction of the article 1A from the left and right leg-holes 11a, 11b into the article 1A.

To assemble the article 1A in FIG. 1 from a state as illustrated in FIG. 3 by an exploded perspective view, the article 1A is folded along a center line L indicated by two-dotted chain line with the inner sheet 2 inside and then the front and rear portions 7a, 7b of the waist member 1a are connected to each other by joining them along the respective side edge portions 7c. Then the first and second tuckable side zones 19, 20 are folded along the first and second imaginary tuckable guide lines 16, 17 and the first and second tuckable side zones 19, 20 are tucked from the left and right leg-holes 11a, 11b into the article 1A as indicated by an arrow W in FIG. 2.

The first and second imaginary tuckable guide lines 16, 17 preferably include therebetween an angle θ in a range of 60-90°, as illustrated in FIG. 3. If the angle θ is smaller than 60°, the first and second tuckable side zones 19, 20 tucked from the left and right leg-holes 11a, 11b into the article 1A will not be conformed to the wearer's crotch area between its thighs and it will be difficult to place the crotch region 33 properly against the wearer's crotch area. If the angle θ exceeds 90°, on the other hand, the first and second imaginary tuckable guide lines 16, 17 will extend to the respective side edge potions 7c of the waist member 1a and, in consequence, it is likely that the side edge portions 7c will be tucked inwardly in the transverse direction of the article 1A.

Figure 4:
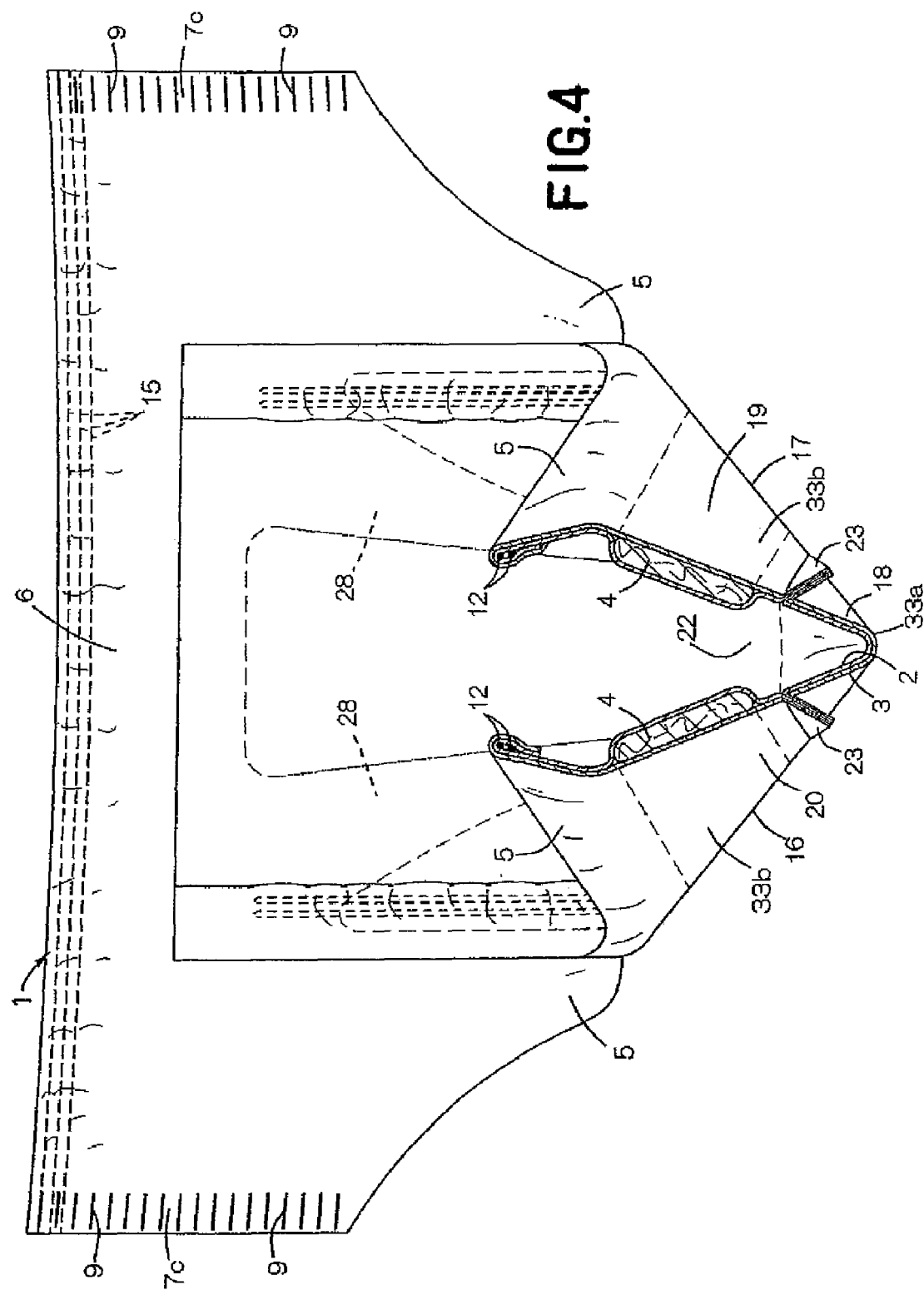
FIG. 4 is a sectional view taken along a line A-A in FIG. 1.
Figure 5:
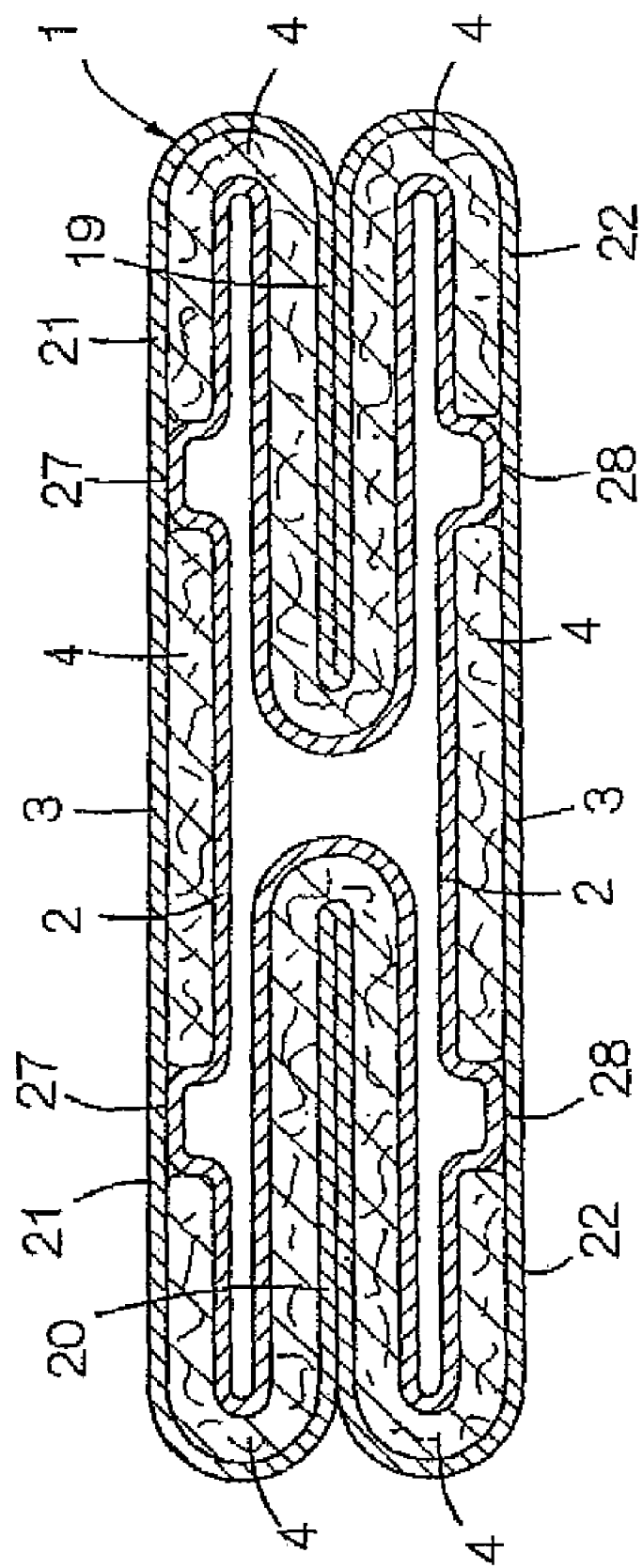
FIG. 5 is a cross-sectional view taken along a line B-B in FIG. 1.

FIG. 4 is a sectional view taken along a line A-A in FIG. 1 and FIG. 5 is a cross-sectional view taken along a line B-B in FIG. 1. The article 1A is formed in the first and second tuckable side zones 19, 20 with the darts 23 and the first and second tuckable side zones 19, 20 are folded along the first and second imaginary tuckable guide lines 16, 17 and tucked from the left and right leg-holes 11a, 11b into the article 1A. Thus, the transverse dimension of the crotch region 33 can be reduced compared to that before the darts 23 are formed and the first and second tuckable side zones 19, 20 are tucked. The crotch region 33 is properly placed against the wearer's crotch area so that the wearer experiences no feeling of discomfort when the article 1A is put on the wearer's body.

As mentioned above, since the article 1A defines the low stiffness middle zone 18 in the transversely middle of the crotch region 33 so the transversely middle zone 33a has stiffness lower than the remaining zone in the article 1A in which the absorbent panel 4 is interposed, it is possible for the article 1A to alleviate a feeling of discomfort possibly experienced by the wearer when this transversely middle zone 33a is placed against the wearer's crotch area.

Upon wearing the article 1A, portions of the article 1A including parts of the absorbent panel 4 in the vicinity of its side edges 4a are tucked in the tuckable guide front and rear zones 27, 28 as the front and rear waist regions 32, 34 are deformed along the wearer's torso a generally annular shape. Consequently, the absorbent panel 4 also is deformed substantially in an annular shape. In this way, the article 1A facilitates the absorbent panel 4 to be conformed to the shape of the individual wearer's torso and enables a zone in which the absorbent panel 4 is interposed, to be placed in close contact with the wearer's skin through the inner sheet 2.

The first and second tuckable side zones 19, 20 rise as they are tucked into the article 1A as illustrated in FIG. 4. The first and second tuckable side zones 19, 20 form barriers against bodily discharges and thereby to prevent bodily discharges from leaking out of the crotch region 33. Decrease in the transverse dimension of the crotch region 33 does not reduce the function of absorbing bodily discharges in the crotch region 33 because portions of the absorbent panel 4 lying in the first and second tuckable side zones 19, 20 absorb and contain bodily discharges.

The outer sheet 3 has its outer surface placed upon each other in the first and second tuckable side zones 19, 20 as the tuckable side zones 19, 20 are tucked as illustrated in FIG. 5. The outer surface of the outer sheet 3 placed upon itself in this manner may be optionally joined to itself so as to be maintained in this state. Furthermore, to maintain the first and second tuckable side zones 19, 20 in a tucked state, it is also possible to place the outer surface of the inner sheet 2 extending in the first tuckable side zone 19, the front and rear zones 21, 22 upon itself, on one hand, and to place the outer surface of the inner sheet 2 extending in the second tuckable side zone 20, the front and rear zones 21, 22 upon itself, on the other hand. The outer surface of the inner sheet 2 placed upon itself in the zones 19, 20, 21, 22 may be optionally joined to itself.

Though not illustrated, the article 1A may be formed with the low stiffness middle zone 18 not only in the transversely middle zone 33a but also in transversely opposite side zones 33b. In this case, the first and second tuckable side zones 19, 20 can be more smoothly tucked from the left and right leg-holes 11a, 11b into the article 1A.

Figure 6:
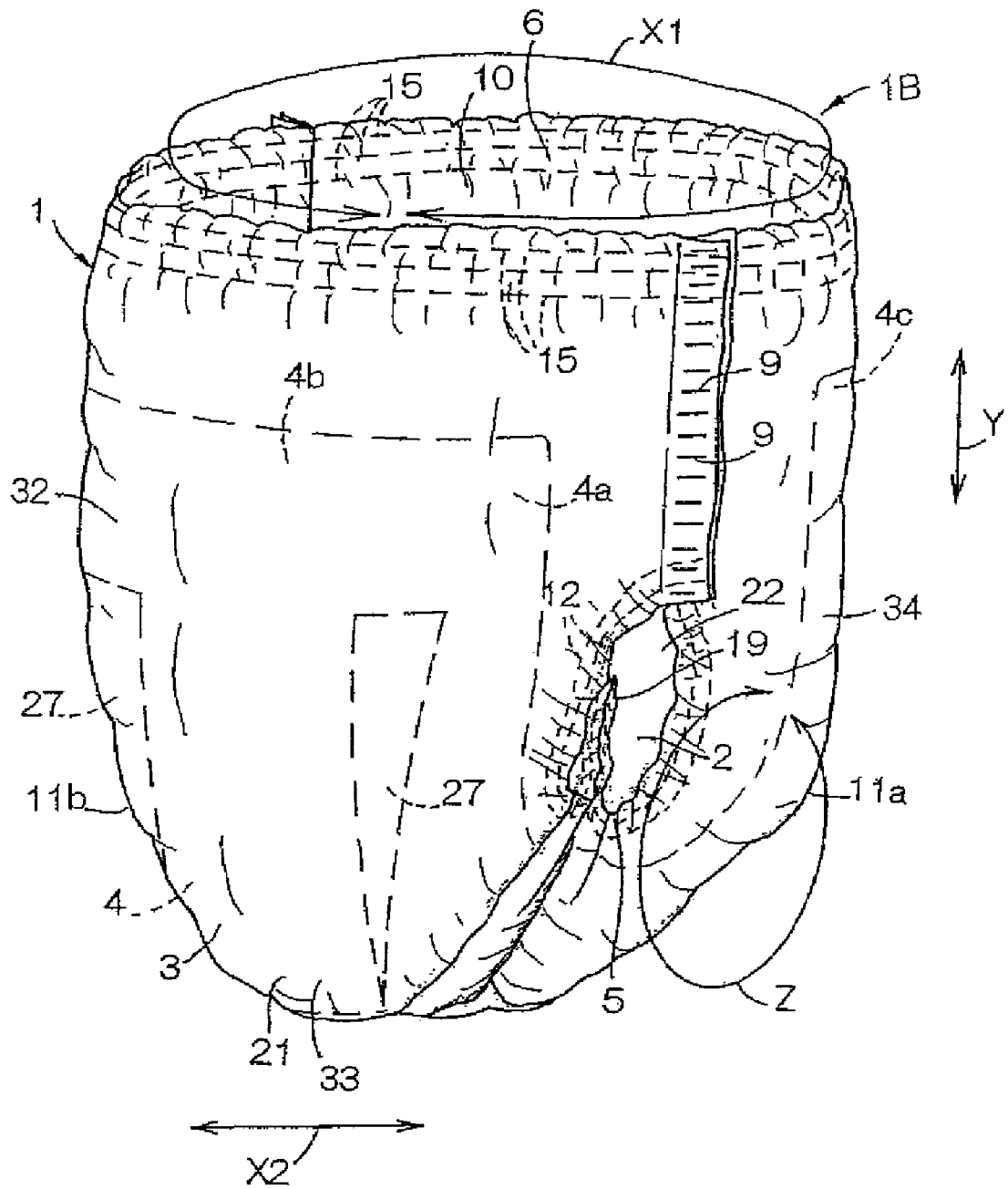
FIG. 6 is a perspective view showing one preferred embodiment of the article according to this invention.
Figure 7:
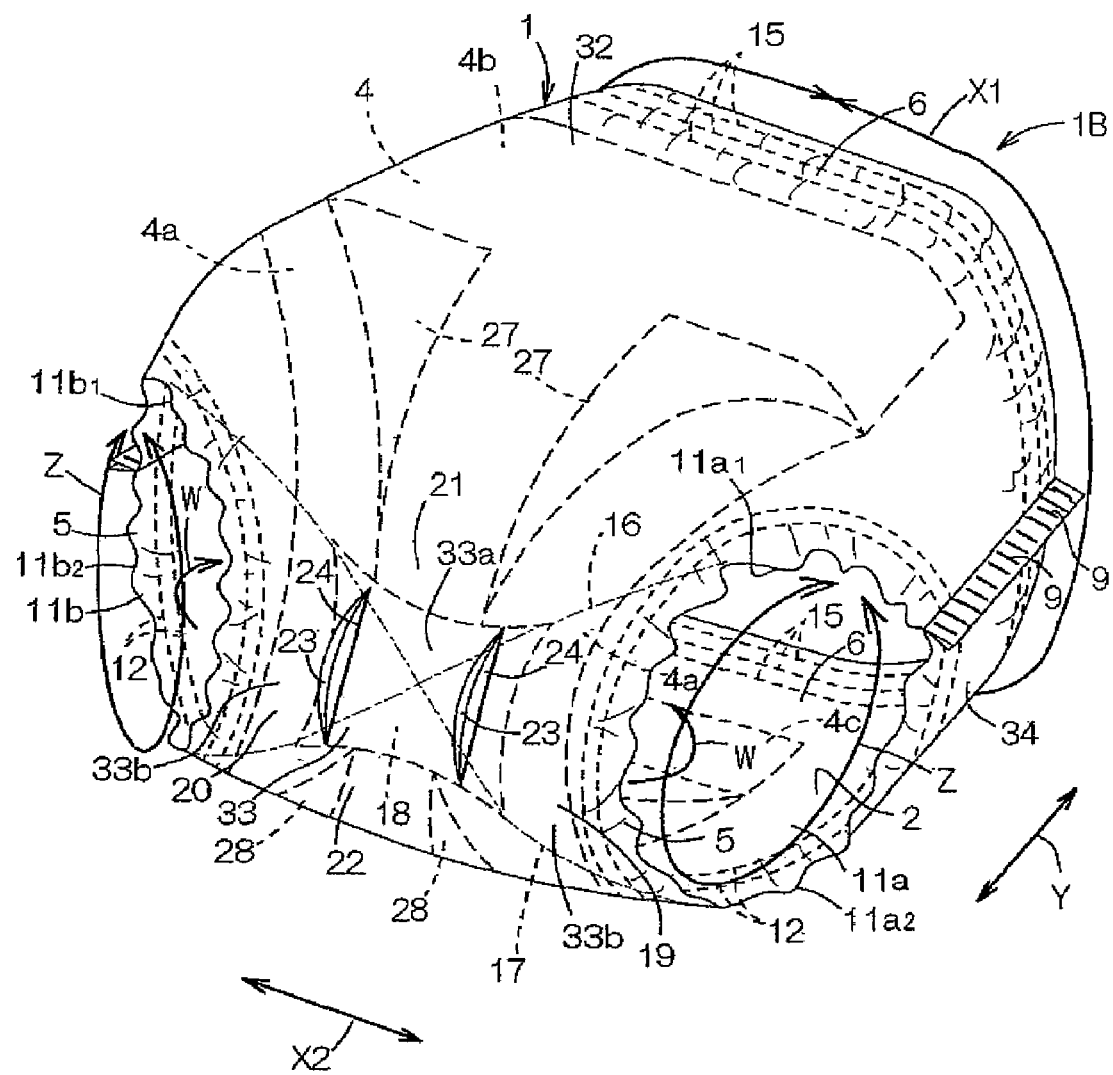
FIG. 7 is a perspective view showing the article of FIG. 6 before the first and second tuckable side zones are tucked from the left and right leg-holes into the article.
Figure 8:
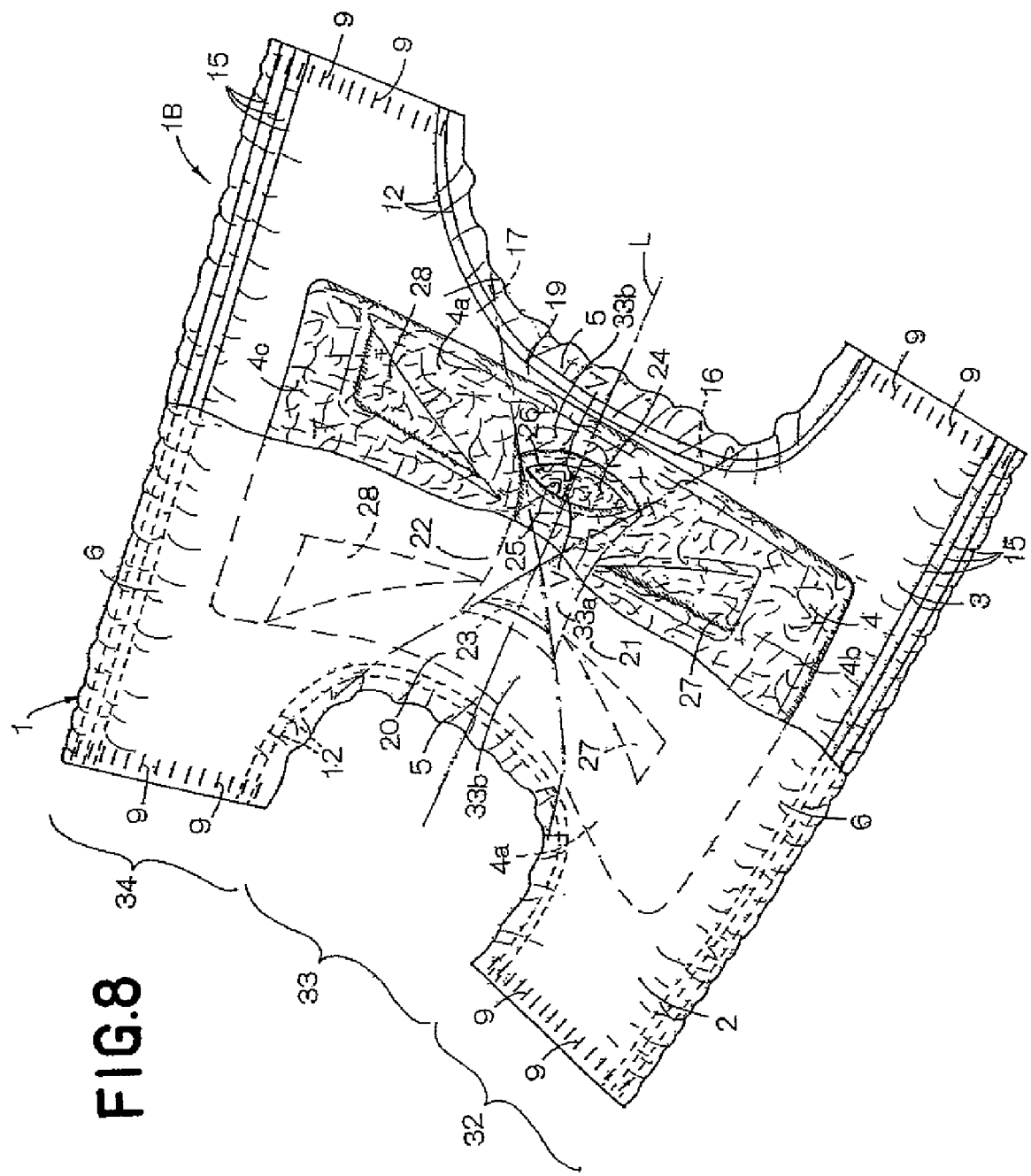
FIG. 8 is an exploded perspective view showing the article of FIG. 6 with the front and rear waist regions disconnected from each other as partially cutaway.

FIG. 6 is a perspective view showing one preferred embodiment of an article 1B according to the invention, FIG. 7 is a perspective view showing the article 1B as before the first and second tuckable side zones 19, 20 are tucked from the left and right leg-holes 11a, 11b into the article 1B and FIG. 8 is an exploded perspective view showing the article 1B of FIG. 6 with the front and rear waist regions 32, 34 disjoined from each other and partially broken away. In FIGS. 6 and 7, the waist-surrounding direction is indicated by an arrow X1, the transverse direction is indicated by an arrow X2, the longitudinal direction is indicated by an arrow Y and the thigh-surrounding direction is indicated by an arrow Z. FIG. 8 illustrates the article 1B before the first tuckable side zone 19 is formed with the darts 23.

This article 1B is similar to the article 1A of FIG. 1 in that the article 1B comprises a flexible chassis 1 including the liquid-pervious inner sheet 2 defining a body facing side, the liquid-impervious outer sheet 3 defining a garment facing side and the semi-stiff, liquid-absorbent panel 4 interposed between these sheets 2, 3. The crotch region 33 is formed with first and second imaginary tuckable guide lines 16, 17 as indicated by single-dotted chain lines. The article 1B is distinguished from the article 1A in an arrangement as will be described.

While the article 1B also has a transversely narrower dimension in the crotch region 33 than in the front and rear waist regions 32, 34 and has a generally hourglass-like shape as viewed in its plan view, the article 1B is not provided with the waist member la in the article 1A as will be apparent from FIG. 7.

The side flaps 5 in the crotch region 33 are respectively provided with the elastic members 12 each comprising a plurality of elastic strands extending in the thigh-surrounding direction and secured thereto in a stretched state so as to be associated with the leg-holes. The end flaps 6 are respectively provided with the elastic member 15 each comprising a plurality of elastic strands extending in the waist-surrounding direction and secured thereto in a stretched state so as to be associated with the waist-hole. The elastic members 12 associated with the leg-holes and elastic members 15 associated with the waist-hole are disposed between the inner and outer sheets 2, 3 and secured to the respective inner surfaces of the sheets 2, 3.

The side flaps 5 extending in the front and rear waist regions 32, 34 in the longitudinal direction are joined to each other by means of a plurality of heat-sealing lines 9 arranged intermittently in the longitudinal direction. By such joining, the waist-hole 10 and the left and right leg-holes 11a, 11b are formed.

Unlike the article 1A, in the article 1B, the absorbent panel 4 presents also in the tuckable guide middle, front and rear zones 18, 27, 28. Stiffness of the tuckable guide middle, front and rear zones 18, 27, 28 of the crotch region 33 is lower than that in the remaining zone of the article 1B in which the absorbent panel 4 is interposed. The low stiffness zones 18, 27, 28 are defined by making a basic weight thereof less than that in the remaining zone of the absorbent panel 4 and making thickness of the absorbent panel 4 smaller than that in the remaining zone of the absorbent panel 4, respectively.

The first and second tuckable side zones 19, 20 have generally triangles and are folded along the first and second imaginary tuckable guide lines 16, 17 so that the first and second tuckable side zones 19, 20 may be interposed between the front and rear zones 21, 22 and thereby the first and second tuckable side zones 19, 20 are tucked together with the darts 23 inwardly in the transverse direction of the article 1B from the left and right leg-holes 11a, 11b into the article 1B.

To assemble the article 1B of FIG. 6 from a state as illustrated in FIG. 8 by an exploded perspective view, the article 1B is folded along a center line L with the inner sheet 2 inside and then the side flaps 5 extending in the front and rear waist region 32, 34 are joined to each other by joining them. Then the first and second tuckable side zones 19, 20 are folded along the first and second imaginary tuckable guide lines 16, 17 and the tuckable side zones 19, 20 are tucked from the left and right leg-holes 11a, 11b into the article 1B as indicated by the arrow W in FIG. 7.

The article 1B is formed in the first and second tuckable side zones 19, 20 with the darts 23 and the first and second tuckable side zones 19, 20 are folded along the first and second imaginary tuckable guide lines 16, 17 and tucked into the article 1B. Thus, the transverse dimension of the crotch region 33 can be reduced as in the case of the article 1A. The crotch region 33 is properly placed against the wearer's crotch area so that the wearer experiences no feeling of discomfort when put on the wearer's body.

The first and second tuckable side zones 19, 20 including parts of the absorbent panel 4 rise as the first and second tuckable side zones 19, 20 are tucked into the article 1B. The first and second tuckable side zones 19, 20 form barriers against bodily discharges and thereby to prevent bodily discharges from leaking out from the crotch region 33. Decrease in the transverse dimension of the crotch region 33 does not reduce the function of absorbing bodily discharges in the crotch region 33 because portions of the absorbent panel 4 lying in the transversely middle zone 33a as well as the first and second tuckable side zones 19, 20 absorb and contain bodily discharges.

Upon wearing the article 1B, portions of the article 1B including parts of the absorbent panel 4 in the vicinity of its side edges 4a are tucked in the tuckable guide front and rear zones 27, 28 having relatively low stiffness and the absorbent panel 4 is deformed along the wearer's torso in a generally annular shape. In this way, the absorbent panel 4 is easily conformed to a shape of an individual wearer's torso and the chassis 1 and placed in close contact with the wearer's skin through the inner sheet 2.

Though not illustrated, the article 1B may be formed with the low stiffness middle zone 18 not only in the transversely middle zone 33a but also in transversely opposite side zones 33b. In this case, the first and second tuckable side zones 19, 20 can be more smoothly tucked into the article 1B.

Figure 9:
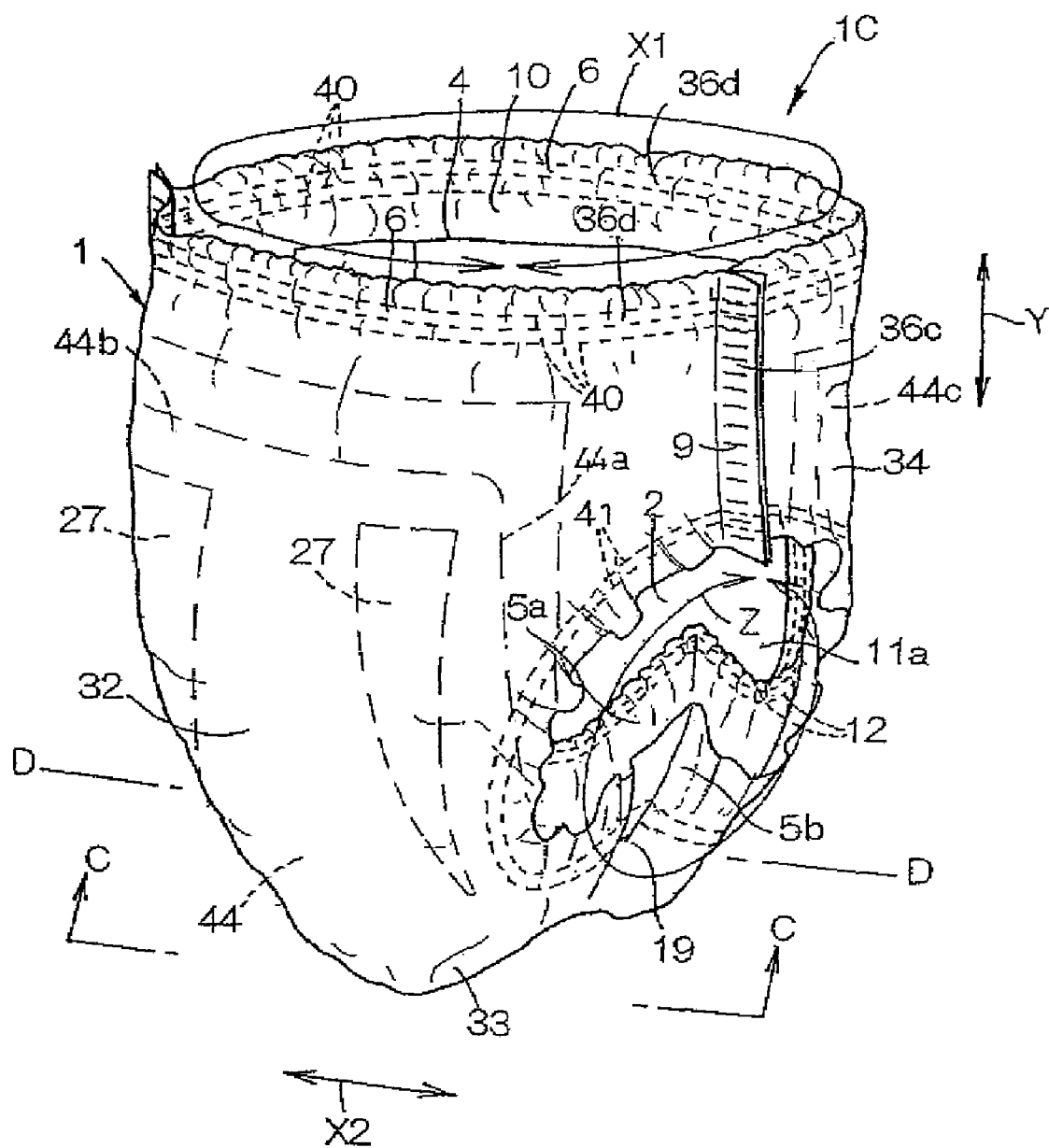
FIG. 9 is a perspective view showing another preferred embodiment of the article according to this invention.
Figure 10:
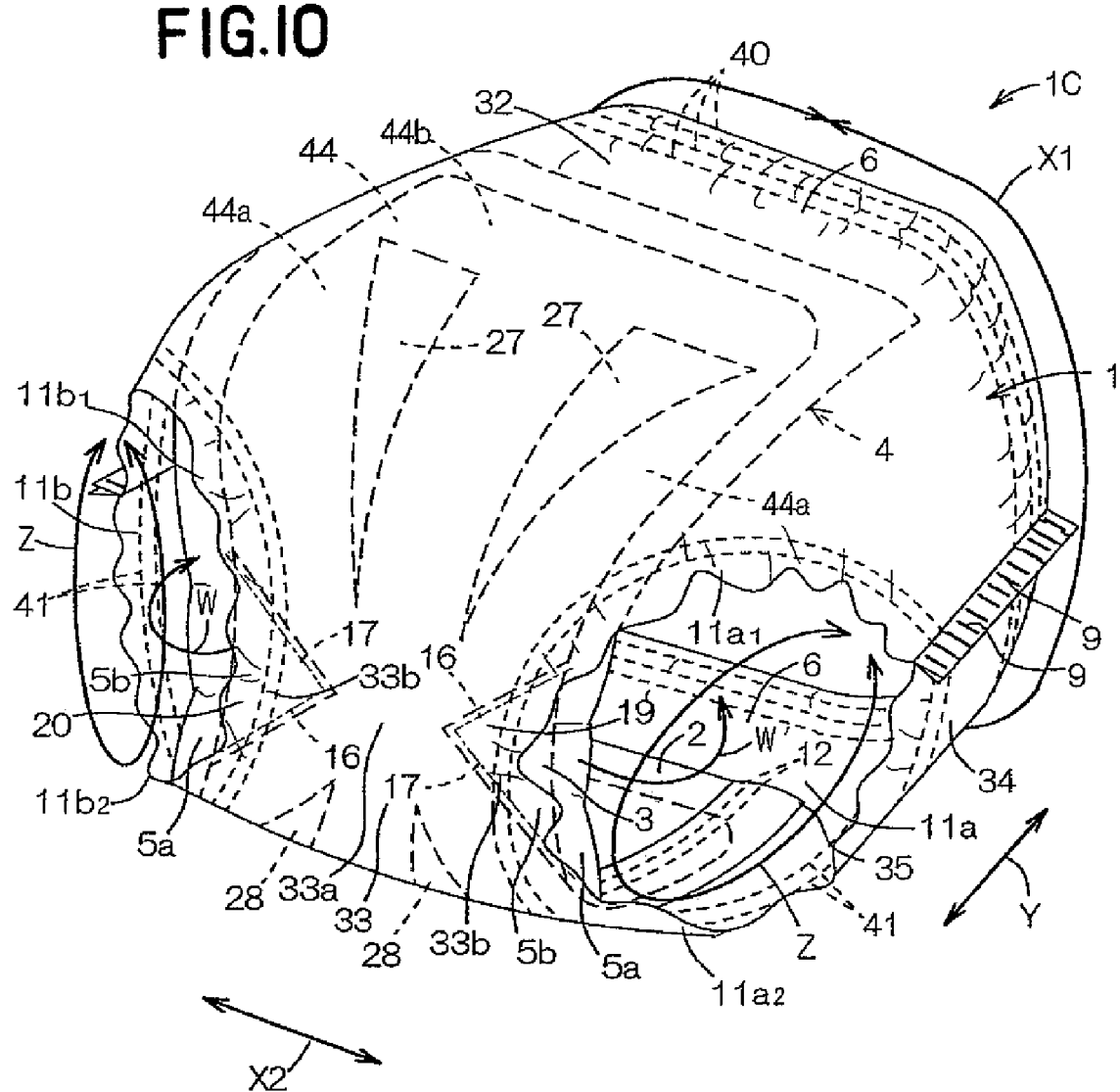
FIG. 10 is a perspective view showing the article of FIG. 9 before the first and second tuckable side zones are tucked from the left and right leg-holes into the article.
Figure 11:
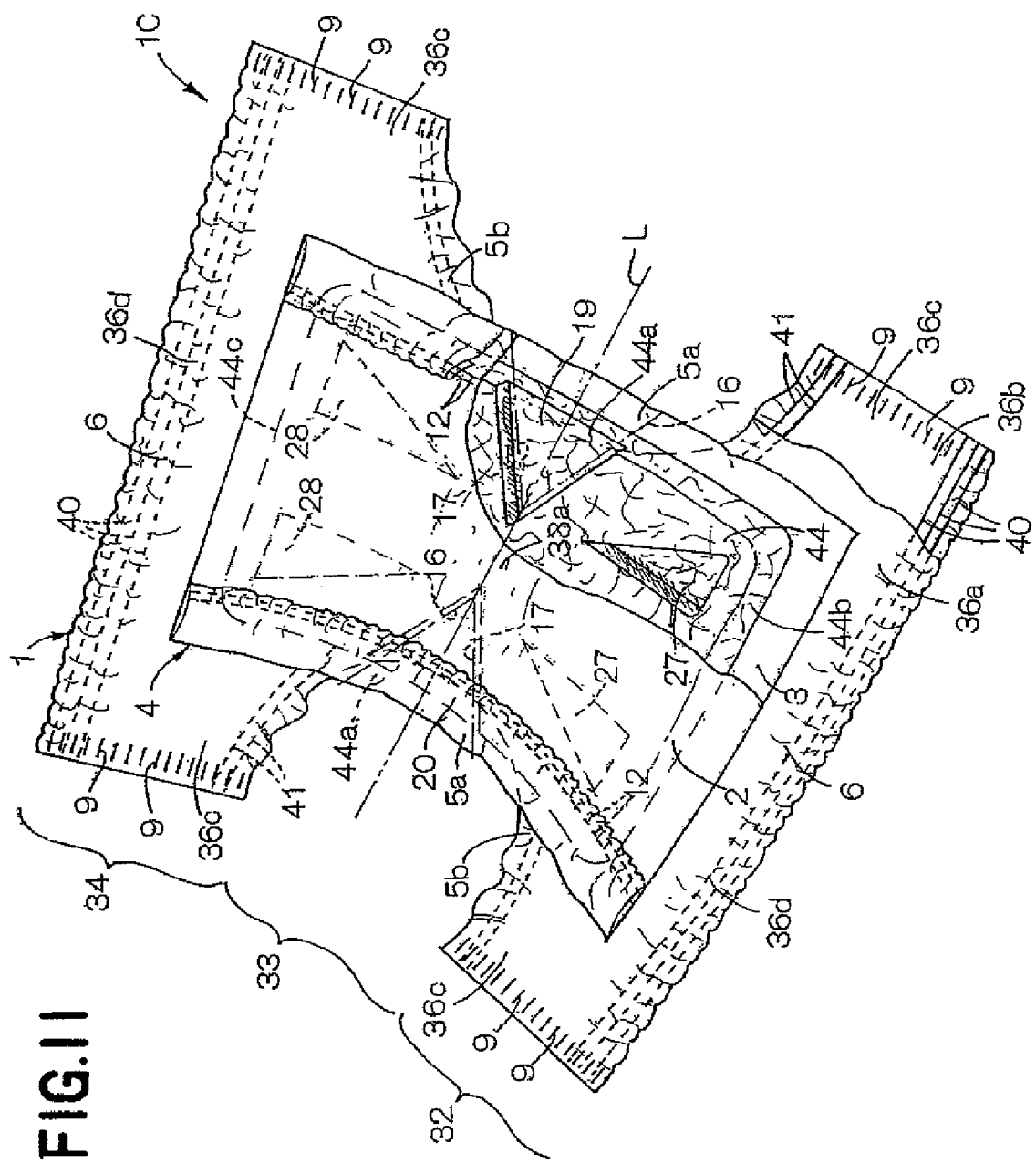
FIG. 11 is an exploded perspective view showing the article of FIG. 10 with the front and rear waist regions disconnected from each other as partially cutaway.

FIG. 9 is a perspective view showing still another preferred embodiment of an article 1C according to this invention. FIG. 10 is a perspective view showing the article 1C in a state before the first and second tuckable side zones 19, 20 are tucked from the left and right leg-holes 11a, 11b into the article 1C and FIG. 11 is an exploded perspective view showing the article 1C in FIG. 10 with the front and rear waist regions 32, 34 disjoined from each other and partially cutaway. In FIGS. 9 and 10, the waist-surrounding direction is indicated by the arrow X1, the transverse direction is indicated by the arrow X2, the longitudinal direction is indicated by the arrow Y and the thigh-surrounding direction is indicated by the arrow Z.

The article 1C comprises a flexible chassis 1 composed of inner and outer sheets 36a, 36b and a semi-stiff, liquid-absorbent panel 4. The absorbent panel 4 is formed separately from the chassis 1 in the form of pad and comprises the liquid-pervious inner sheet 2 defining a body facing side, the liquid-impervious outer sheet 3 defining a garment facing side and a liquid-absorbent core 44 disposed between the inner and outer sheet 2, 3 and joined to the inner surface of at least one of the two sheets 2, 3. The chassis 1 has an area larger than those of the inner and outer sheets 2, 3 and a generally hour glass-shape as viewed in its plan view. The absorbent panel 4 is intermittently joined to the inner sheet 36a of the chassis 1.

With respect to the configuration, the chassis 1 is composed of the front and rear waist regions 32, 34 opposed to each other and the crotch region 33 extending between these waist regions 32, 34. The article 1C has a pair of side flaps 5a formed by portions of the inner and outer sheets 2, 3 lying outside the transversely opposite side edges 44a of the core 44 and a pair of side flaps 5b formed by portions of the chassis 1 lying outside the transversely opposite side edges 44a of the core 44, so as to extend in the thigh-surrounding direction, respectively, and a pair of end flaps 6 formed by portions of the chassis 1 lying outside the longitudinally opposite front and rear ends 44b, 44c of the core 4 so as to extend in the waist-surrounding direction in the front and rear waist regions 32, 34, respectively.

The side flaps 5a in the absorbent panel 4 are respectively provided with elastic members 12 each comprising a plurality of elastic strands extending in the thigh-surrounding direction and strands to the outer surface of the inner sheet 2 in a stretched state so that these elastic members 12 are associated with the respective leg-holes.

Transversely opposite side edge portions 36c, 36c of the chassis 1 extending in the longitudinal direction in the front and rear waist regions 32, 34 are overlaid and joined together by means of a plurality of heat-sealing lines 9 arranged intermittently in the longitudinal direction. By such joining, the waist-hole 10 and the left and right leg-holes 11a, 11b are formed.

The chassis 1 are formed of a breathable composite nonwoven fabric consisting of two layers 36a, 36b of substantially non-stretchable hydrophobic fibrous nonwoven fabric. The chassis 1 is provided along its longitudinally opposite end portions 36d, 36d with elastic members 40 each comprising a plurality of elastic strands extending in the waist-surrounding direction and secured thereto in a stretched state so as to be associated with the waist-hole. The side flaps 5b in the chassis 1 are provided along the respective transversely opposite side edge portions 36c extending in the crotch region 33 with elastic members 41 each comprising a plurality of elastic strands extending in the thigh-surrounding direction and bonded thereto in a stretched state so as to be associated with the leg-holes. The elastic members 40, 41 associated with the waist-hole and the leg-holes, respectively, are interposed between the two layers 36a, 36b of nonwoven fabric forming the chassis 1 and secured to the layers 36a, 36b.

As indicated by single-dot-chain lines in FIGS. 10 and 11, the crotch region 33 is formed with a first imaginary tuckable guide line 16 and a second imaginary tuckable guide line 17 both extending in the transverse direction. The crotch region 33 is formed in its transversely opposite side portions 33b with the first and second tuckable side zones 19, 20 having stiffness lower than that in the remaining zone of the article 1C in which the core 44 is interposed. The first tuckable side zone 19 is defined by the peripheral edge of the left leg-hole 11a and the first and second imaginary tuckable guide lines 16, 17 and the second tuckable side zone 20 is defined by the peripheral edge of the right leg-hole 11b and the first and second imaginary tuckable guide lines 16, 17. The first and second tuckable zones 19, 20 have generally triangles and are defined by making a basic weight thereof and making thickness of the core 44 smaller than that in the remaining zone of the core 44.

The first imaginary tuckable guide line 16 extends from the peripheral edge 11a1 of the left leg-hole 11a lying in the front waist region 32 and the peripheral edge 11b2 of the right leg-hole 11b lying in the rear waist region 34 toward the transversely middle zone 33a of the crotch region 33. The second imaginary tuckable guide line 17 extends from the peripheral edge 11b1 of the right leg-hole 11b lying in the front waist region 32 and the peripheral edge 11a2 of the left leg-hole 11a lying in the rear waist region 34 toward the transversely middle zone 33a of the crotch region 33. The imaginary tuckable guide lines 16, 17 are formed in the first and second tuckable side zones 19, 20 defined in the transversely opposite side portions 33b of the crotch region 33.

Inside the side edges 44a of the core 44, the pair of tuckable front guide zones 27 and the pair of tuckable guide rear zones 28 are formed. The tuckable guide front zones 27 are defined between the transversely middle zone 33a of the crotch region 33 and the front end 4b of the core 44 lying in the front waist region 32 and extend in the thigh-surrounding direction. The tuckable guide rear zones 28 are defined between the transversely middle zone 33a of the crotch region 33 and the rear end 44c of the core 4 lying in the rear waist region 34 and extend in the thigh-surrounding direction. Stiffness of the core 44 in the zones 19, 20, 27, 28 is lower than its remaining zone and consequently the zones 19, 20, 27, 28 are low stiffness zones. The low stiffness zones 27, 28 are defined by making a basic weight thereof and making thickness of the core 44 smaller than that in the remaining zone of the core 44.

The first and second tuckable side zones 19, 20 are tucked inwardly in transverse direction of the article 1C along the first and second imaginary tuckable guide lines 16, 17 into the article 1C. The article 1C is distinguished from the articles 1A, 1B in that the darts are not formed in the first and second tuckable side zones 19, 29 are formed with none of the darts.

To assemble the article 1C of FIG. 9 from a state as illustrated in FIG. 11 in by exploded perspective view, the article 1C is folded along a center line L with the inner sheet 2 inside and then the chassis 1 extending in the front and rear waist regions 32, 34 are joined to each other by joining them along the respective side edge portions 36c, 36c. Then the first and second tuckable side zones 19, 20 are folded along the first and second imaginary tuckable guide lines 16, 17 and the first and second tuckable side zones 19, 20 are tucked from the left and right leg-holes 11a, 11b into the article 1C as indicated by the arrow W in FIG. 10.

Figure 12:
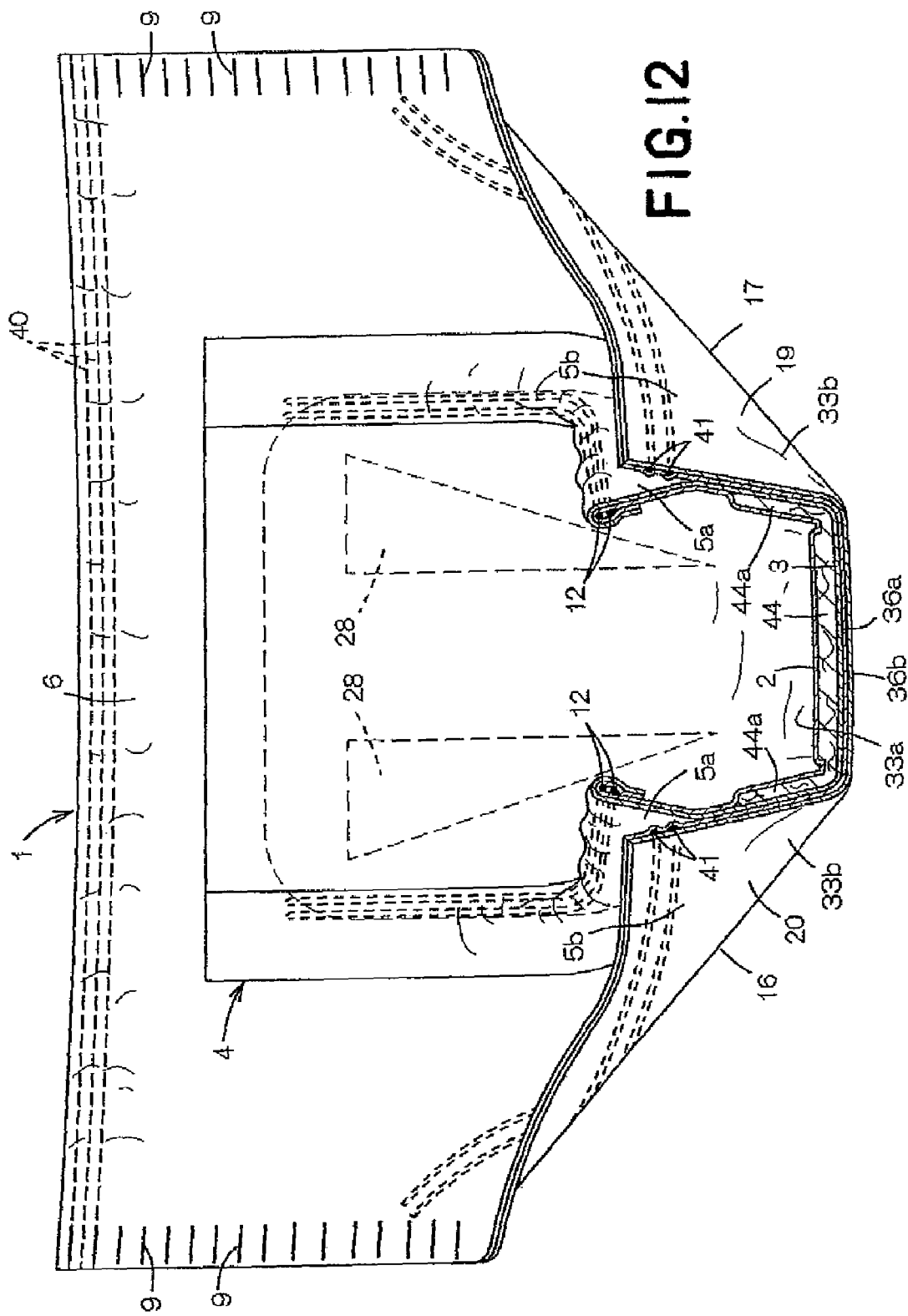
FIG. 12 is a sectional view taken along a line C-C in FIG. 9.
Figure 13:
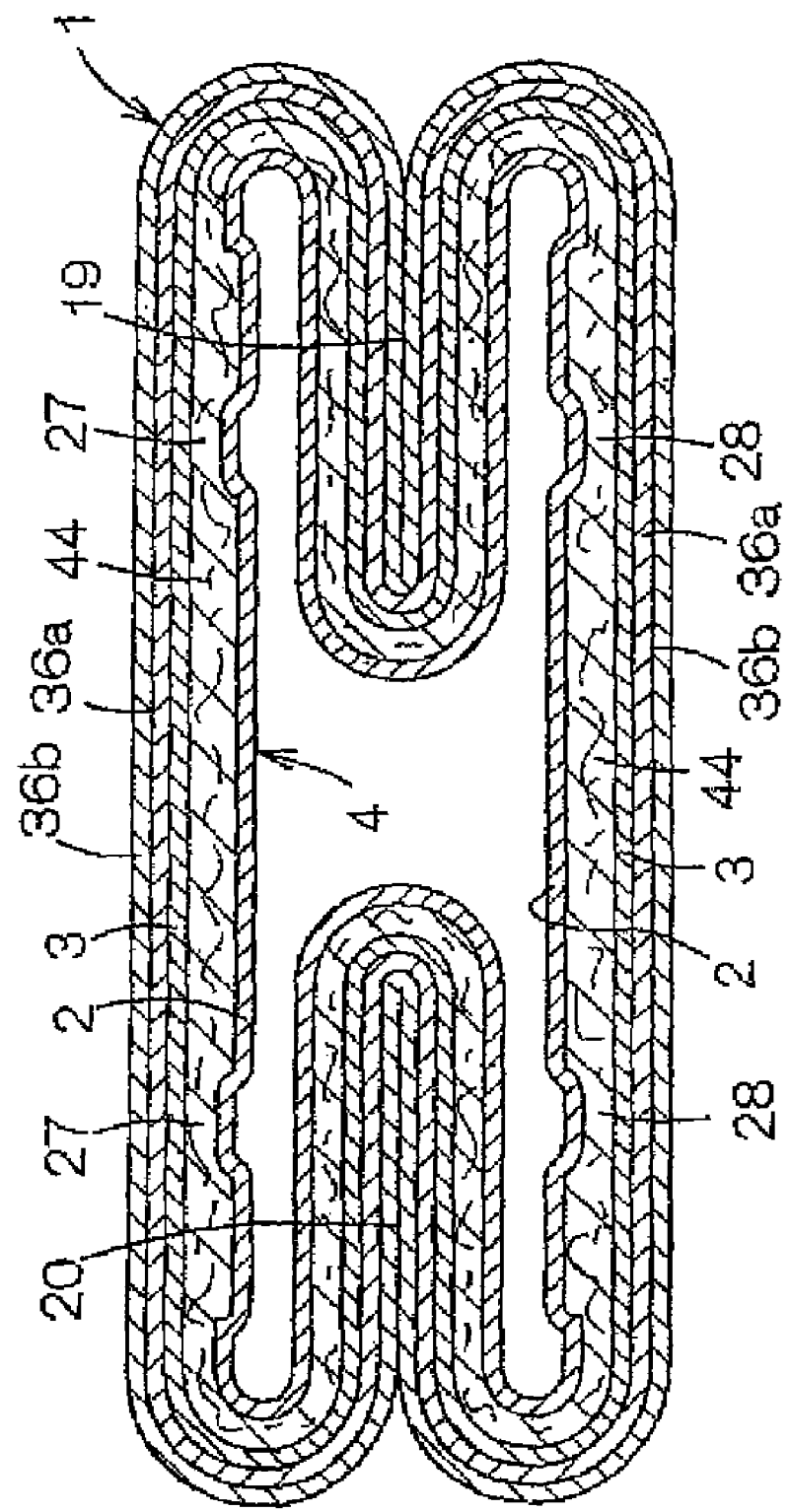
FIG. 13 is a cross-sectional view taken along a line D-D in FIG. 9.

FIG. 12 is a sectional view taken along a line C-C in FIG. 9 and FIG. 13 is a cross-sectional view taken along a line D-D in FIG. 9. The first and second tuckable side zones 19, 20 are folded along the first and second imaginary tuckable guide lines 16, 17 and tucked from the left and right leg-holes 11a, 11b in the article 1C. Thus, the transverse dimension of the crotch region 33 can be reduced similarly to the articles 1A and 1B shown in FIG. 1 and FIG. 6, respectively. Upon wearing this article 1C, the crotch region 33 is properly placed against the wearer's crotch area so that the wearer experiences no feeling of discomfort.

The first and second tuckable side zones 19, 20 including the core 44 rise as the first and second tuckable side zones 19, 20 are tucked from the left and right leg-holes 11a, 11b into the article 1C, as illustrated in FIG. 9. The first and second tuckable side zones 19, 20 form barriers against bodily discharges and thereby to prevent bodily discharges from leaking out from the crotch region 33. Decrease in the transverse dimension of the crotch region 33 does not reduce the function of the core 44 in the crotch region 33 to absorb bodily discharges because portions of the core 44 lying in the transversely middle zone 33a and the first and second tuckable side zones 19, 20 of the crotch region 33 absorb and contain bodily discharges.

Upon wearing the article 1C, portions of the article 1C including parts of the core 44 in the vicinity of its side edges 44a are tucked in the tuckable guide front and rear zones 27, 28 deformed along the wearer's torso in a generally annular shape. Consequently, the core 44 also is deformed substantially in an annular shape. In this way, the article 1C facilitates the core 44 to be conformed to a shape of the individual wearer's torso and enables a zone in which the core 44 is interposed, to be placed in close contact with the wearer's skin through the inner sheet 2.

Also for the articles 1A, 1B shown by FIGS. 1 and 6, respectively, it is not essential to form the first and second tuckable side zones 19, 20 with the darts 23. In the articles 1A, 1B, 1C having been illustrated and described, any one of the tuckable guide front and rear zones 27, 28 may be eliminated and even both of them may be eliminated.

The inner sheet 2 may be formed of material selected from a group of material including a hydrophilic fibrous nonwoven fabric, a hydrophobic fibrous nonwoven fabric having a plurality of fine apertures and plastic film having a plurality of fine pores.

The outer sheet 3 may be formed of material selected from a group of materials including a substantially non-stretchable hydrophobic fibrous nonwoven fabric, substantially non-stretchable breathable but liquid-impervious plastic film, a composite nonwoven fabric including a laminate of these hydrophobic fibrous nonwoven fabric layers, and a composite sheet comprising a laminate of these hydrophobic fibrous nonwoven fabric and breathable but liquid-impervious plastic film. The waist member 1a may be formed of the same sheet material as the outer sheet 3. The chassis 1 may be formed of material selected from a group of materials including substantially non-stretchable hydrophobic fibrous nonwoven fabric, substantially non-stretchable breathable but liquid-impervious plastic film and a composite sheet consisting of such hydrophobic fibrous nonwoven fabric and breathable but liquid-impervious plastic film laminated with each other. It is also possible to form the outer sheet 3, the waist member 1a and the chassis 1 comprising a composite nonwoven fabric with both sides of the surface of a fibrous nonwoven fabric made by melt blown method having highly water-resistant property sandwiched by a fibrous nonwoven fabric by spun bond method having high strength and flexibility.

Nonwoven fabric may be selected from a group of materials including products obtained by spun lacing, needle punching, melt blowing, thermal bonding, spun bonding, chemical bonding and air-through processes. Component fiber of the nonwoven fabric may be selected from a group of materials including polyolefine-, polyester- and polyamide-based fibers and core-sheath-type and side-by-side-type conjugated fibers of polyethylene/polypropylene and polyethylene/polyester.

It is also possible to use a stock material for the chassis 1 selected from a group of materials consisting of a stretchable and hydrophobic fibrous nonwoven fabric, stretchable and liquid-impervious plastic film, and a composite sheet comprising stretchable and liquid-impervious fibrous nonwoven fabric and stretchable and liquid-impervious plastic film laminated with each other. The stretchable fibrous nonwoven fabric may be a product obtained by melt blowing or spun bonding process. Component fiber of the stretchable nonwoven fabric may be a stretchable fiber obtained by melting and spinning thermoplastic elastomer resin.

It is also possible to form the chassis 1 using a composite nonwoven fabric comprising a hydrophobic fibrous nonwoven fabric made of a crimped fiber obtained by a melt spinning thermoplastic synthetic resin and placed upon at least one surface of a stretchable and hydrophobic fibrous nonwoven fabric made of a thermoplastic elastomer resin fiber.

Bonding of sheet members in the embodiments of this invention and securing of the elastic members to the sheet members may be carried out using a hot melt adhesive of welding technique such as heat-sealing and sonic-sealing.

The disposable pull-on wearing article according to this invention can reduce the transverse dimension of the crotch region in comparison to the wearing article of prior art or the wearing article currently available in the market by folding the first and second tuckable side zones of the crotch region along the first and second imaginary tuckable guide lines and tucking them into the left and right leg-holes. Upon wearing this article, the crotch region is properly placed in close contact with the wearer's crotch region without creating any feeling of discomfort against the wearer. With this article, the first and second tuckable side zones rise toward the waist-hole as the first and second tuckable side zones are tucked into the left and right leg-holes so that the first and second zones may form barriers against bodily discharges and prevent bodily discharges from leaking out from the crotch region.

The embodiment so arranged that the transversely middle and/or transversely opposite sides of the crotch region is or are formed with the low stiffness zones. Facilitates the first and second tuckable side zones to be folded along the first and second imaginary tuckable guide lines and to be tucked from the left and right leg-holes into the article.

The embodiment in which the first and second tuckable side zones are formed with a pair of darts extending in the crotch region in the thigh-surrounding direction can further reduce the transverse dimension of the crotch region.

The embodiment formed with the tuckable guide front and rear zones extending inside the transversely opposite side edges of the absorbent panel or core in the waist-surrounding direction facilitates the absorbent panel or core to be conformed to the torso shape of the individual wearer in close contact with the wearer's skin. This is because that the side edges of the absorbent panel or core are folded in these tuckable guide front and rear zones and the absorbent panel or core having stiffness higher than that of the inner and outer sheet and the chassis can be deformed along the wearer's torso substantially in an annular shape.

The invention claimed is:

1. A disposable pull-on wearing article, comprising:
opposite body-facing and garment-facing surfaces;
a front waist region, a rear waist region, a crotch region extending in a longitudinal direction of said article between the front and rear waist regions;
said waist regions being permanently at transversely opposite sides thereof to define a waist hole and a first and second leg-holes;
a pad containing therein absorbent material and extending from the front waist region to the rear waist region via the crotch region, wherein said pad has front and rear end edges opposed in the longitudinal direction of the article, and first and second side edges opposed in a transverse direction of the article and connecting the front and rear end edges;
a pair of oblique first folding lines converging from a peripheral edge of the first leg-hole toward a quadrilateral middle zone of said pad in the crotch region; and
a pair of oblique second folding lines converging from a peripheral edge of the second leg-holes toward the quadrilateral middle zone of said pad in the crotch region;
wherein
said crotch region includes a first side portion associated with the first leg-hole, folded along the first folding lines, and tucked inwardly of the article to define a first inward tuck;
said crotch region further includes a second side portion associated with the second leg-hole, folded along the second folding lines, and tucked inwardly of the article to define a second inward tuck;

a stiffness of said pad in the quadrilateral middle zone and outside said first and second folding lines is less than in a remaining zone of said pad, said remaining zone being located outside said quadrilateral middle zone;

said pad has front and rear sections which are neither folded nor tucked, and said pad further comprises at least one selected from the group consisting of first and second front zones having a stiffness lower than that in the remaining zone of said pad, said remaining zone being located outside said quadrilateral middle zone and said first and second front zones, said first and second front zones being entirely located in the front section and between the front end edge of said pad and the first and second inward tucks, respectively; and first and second rear zones having a stiffness lower than that in the remaining zone of said pad, said remaining zone being located outside said quadrilateral middle zone and said first and second rear zones, said first and second rear zones being entirely located in the rear section and between the rear end edge of said pad and the first and second inward tucks, respectively; and the first and second front zones and/or the first and second rear zones are free of said absorbent material.

2. A disposable pull-on wearing article, comprising:

opposite body-facing and garment-facing surfaces;

a front waist region, a rear waist region, a crotch region extending in a longitudinal direction of said article between the front and rear waist regions;

said waist regions being permanently at transversely opposite sides thereof to define a waist hole and a first and second leg-holes;

a pad containing therein absorbent material and extending from the front waist region to the rear waist region via the crotch region, wherein said pad has front and rear end edges opposed in the longitudinal direction of the article, and first and second side edges opposed in a transverse direction of the article and connecting the front and rear end edges;

a pair of oblique first folding lines converging from a peripheral edge of the first leg-hole toward a quadrilateral middle zone of said pad in the crotch region; and a pair of oblique second folding lines converging from a peripheral edge of the second leg-holes toward the quadrilateral middle zone of said pad in the crotch region;

wherein said crotch region includes a first side portion associated with the first leg-hole, folded along the first folding lines, and tucked inwardly of the article to define a first inward tuck;

said crotch region further includes a second side portion associated with the second leg-hole, folded along the second folding lines, and tucked inwardly of the article to define a second inward tuck;

a stiffness of said pad in the quadrilateral middle zone and outside said first and second folding lines is less than in a remaining zone of said pad, said remaining zone being located outside said quadrilateral middle zone;

said pad has front and rear sections which are neither folded nor tucked, and said pad further comprises at least one selected from the group consisting of first and second front zones having a stiffness lower than that in the remaining zone of said pad, said remaining zone being located outside said quadrilateral middle zone and said first and second front zones, said first and second front zones being entirely located in the front section and between the front end edge of said pad and the first and second inward tucks, respectively; and first and second rear zones having a stiffness lower than that in the remaining zone of said pad, said remaining zone being located outside said quadrilateral middle zone and said first and second rear zones, said first and second rear zones being entirely located in the rear section and between the rear end edge of said pad and the first and second inward tucks, respectively; and the absorbent material in the remaining zone of said pad is thicker than and surrounds the absorbent material in the first and second front zones and/or the first and second rear zones.

* * * * *